United States Patent [19]

Mancarella

[11] Patent Number: 5,601,528
[45] Date of Patent: Feb. 11, 1997

[54] OBSTETRIC DEVICE

[76] Inventor: Donatello Mancarella, Auf dem Kämpchen 33, 42699 Solingen, Germany

[21] Appl. No.: 415,439

[22] Filed: Apr. 3, 1995

[51] Int. Cl.$^6$ ........................................ A61H 19/00
[52] U.S. Cl. ........................... 601/45; 5/602; 128/845
[58] Field of Search .................. 601/45; 128/845; 606/119; 5/602; D24/123

[56] References Cited

U.S. PATENT DOCUMENTS

| D. 263,336 | 3/1982 | Nielsen | D24/123 |
| D. 270,018 | 8/1983 | Knight | D24/123 |
| 2,396,516 | 3/1946 | Lewis | 128/845 |
| 4,080,968 | 3/1978 | Nielsen | 606/119 |
| 4,180,062 | 12/1979 | Alberti et al. | 5/602 |
| 4,703,975 | 11/1987 | Roberts et al. | 5/602 |

FOREIGN PATENT DOCUMENTS

| 560273 | 9/1993 | European Pat. Off. | 601/45 |
| 8900333 | 9/1990 | Netherlands | 128/845 |
| 9000043 | 1/1990 | WIPO | 601/41 |

*Primary Examiner*—Jerome Donnelly
*Assistant Examiner*—Jeanne M. Clark
*Attorney, Agent, or Firm*—Fildes & Outland, P.C.

[57] ABSTRACT

Figure 1:
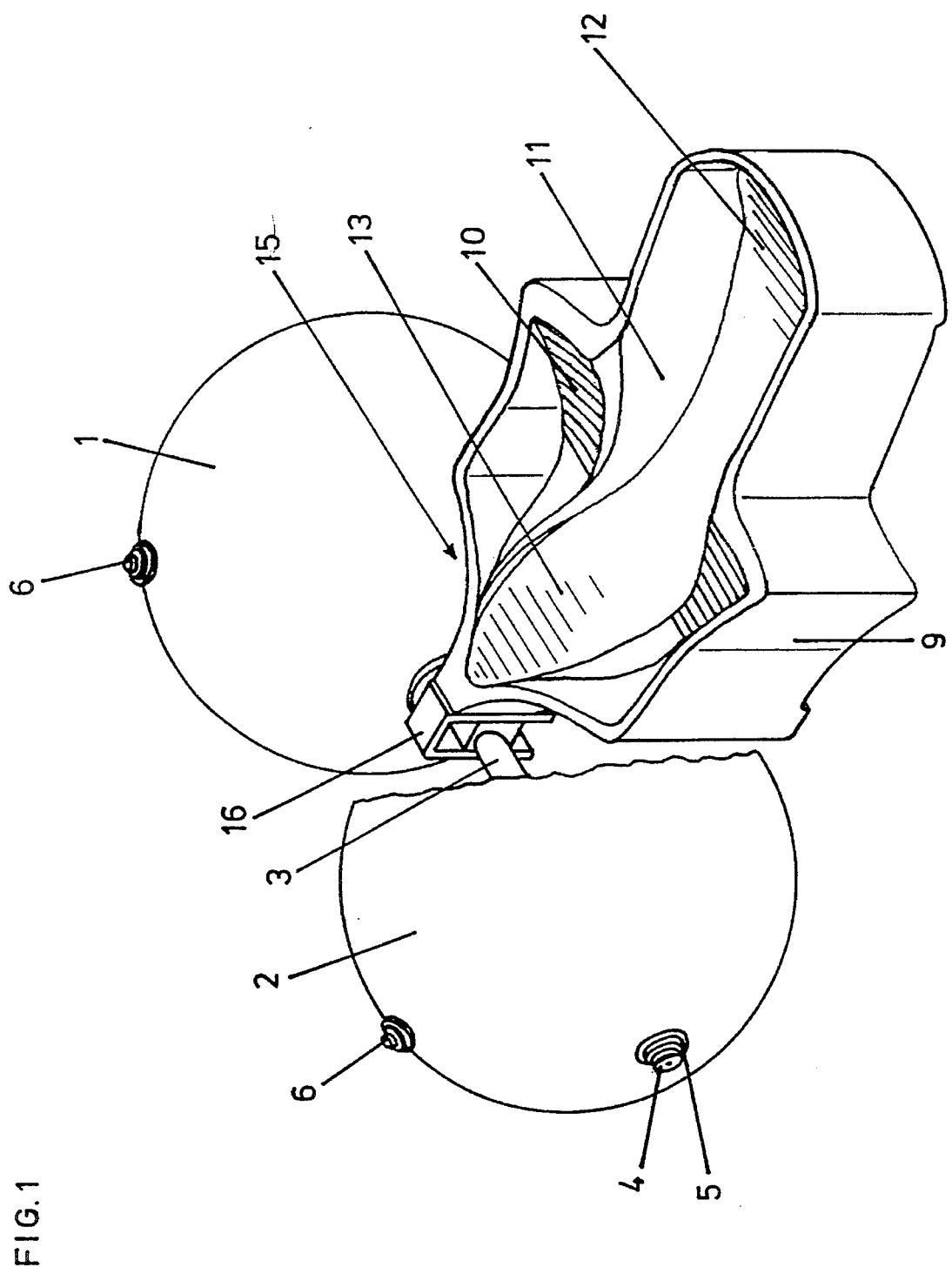

The obstetric device according to the invention has two balloon or ring-shaped bodies (1, 2) of essentially identical design, which are positioned on an axis which runs in the horizontal direction when positioned for use, where the upper sections of the bodies (1, 2) are separated from one another by a gap (8) which narrows in the downward direction and their top sides form a seat (7) for a parturient sitting on the two bodies (1, 2), and a pedestal-like base (9) which can be positioned in an essentially stable, fixed spatial relationship to the bodies (1, 2), and has footrests (10) on which the feet of the parturient can be supported. In a preferred practical example, the pedestal-like base (9) has a fluid-tight catch basin (11) and a projection (16) which reaches over and behind the bar (3) connecting the bodies (1, 2) to one another. The obstetric device enables the parturient to assume a relaxed position during childbirth and a secure and gentle birth for the child to be born. (FIG. 1)

11 Claims, 3 Drawing Sheets

OBSTETRIC DEVICE

The invention relates to an obstetric device for facilitating childbirth and relieving the parturient while giving birth.

It is known practice to use relaxation devices, such as that described in DE-PS 42 07 540 C2, as early as the preparatory phase of childbirth. A relaxation device of this kind particularly serves to massage and relax the muscles of the pelvic floor during the phases before birth, and thus to improve the management of the pain caused by dilation in the pelvic floor region. In this context, the relaxation device consists of two essentially identical balloon or ring-shaped elastic bodies, which are arranged in an essentially rotationally symmetrical manner around an axis which forms the connecting line between the bodies and runs in the horizontal direction when positioned for use. In this context, the bodies are arranged and connected to one another in such a way that, when set down on a floor surface, their upper sections are separated from one another by a gap which narrows in the downward direction and their top sides form a seat on which the parturient can sit. The relaxation of the muscles of the pelvic floor desirable for the mechanical aspects of labour, and gentle horizontal traction on the gluteal muscles, are achieved by moving the pelvis of the parturient, sitting on both bodies. It is thus possible to autogenically train the exerted pelvic floor muscles and, through the rhythmic movements of the parturient on the two balloon-shaped bodies, to improve management of the dilation pain in the pelvic floor region during the bearing-down phase.

The relaxation device only serves to relax the parturient during the preparatory phase of childbirth. However, it is not possible to facilitate childbirth with this device.

The task of the present invention is thus to design an obstetric device which enables the secure positioning of the parturient during childbirth itself, in which the parturient can assume a relaxed position which facilitates childbirth and in which childbirth can be carried out in the most gentle manner possible for the child to be born.

According to the invention, the task is solved in that the obstetric device has two balloon or ring-shaped bodies of essentially identical design, which are positioned on an axis which forms the connecting line between the two bodies and runs in the horizontal direction when positioned for use, where the bodies are arranged and connected to one another in such a way that, when set down on a floor surface, their upper sections are separated from one another by a gap which narrows in the downward direction and their top sides form a seat on which the parturient can sit and where a pedestal-like base is also provided which can be positioned in an essentially stable, fixed spatial relationship to the balloon or ring-shaped bodies, where the pedestal-like base has footrests on which the feet of the sitting parturient can be supported.

Optimum childbirth preparation of the parturient sitting on the seat of the bodies is enabled in the manner described above via the balloon or ring-shaped bodies. When the bearing-down phase begins, the pedestal-like base can be positioned in a fixed manner in relation to the balloon or ring-shaped bodies described above, where the stable positioning of the pedestal-like base simultaneously achieves a fixed arrangement of the balloon or ring-shaped bodies and thus of the seat for the parturient. By supporting the feet of the parturient on the footrests of the pedestal-like base, the parturient assumes an ergonomic position, i.e. one which enables relaxation of the pelvic floor muscles, where the supporting of the feet enables the parturient to exert contact pressure on the seat surface. This guarantees secure positioning of the parturient and simultaneously also facilitates the bearing-down procedure. The childbirth procedure is further facilitated in that the parturient assumes a primarily seated position. As the height of the parturient can vary to some extent, the pedestal-like base can also have several footrests arranged at various distances from the seat, or be provided with means by which the distance and position of the footrests relative to the seat can be changed.

The pedestal-like base expediently has a catch basin for the child to be born so that, during birth, the child is passed into the catch basin together with the amniotic fluid in accordance with the aptonomy theory and is thus not subject to a traumatic transition during birth due to the drastic changes in its immediate environment.

In this context, the catch basin can be designed to collect fluids, such as amniotic fluid or blood, in a fluid-tight manner so that they can be directly and completely collected in the catch basin.

The catch basin expediently has a slanted surface on the end facing the balloon or ring-shaped bodies which rises towards the balloon or ring-shaped bodies and is shaped in such a way that the child to be born can safely slide from the parturient sitting on the seat onto the slanted surface and into the catch basin. Safe childbirth which is gentle on the child and the simplified handling of the baby by the obstetrician are guaranteed in this way.

The footrests for the parturient are expediently positioned inside the catch basin. In this context, the footrests can also be located on projecting areas of the catch basin, or in specially shaped depressions in the catch basin, and dimensioned in such a way that the parturient sitting on the seat can assume different positions. Several separate footrests can also be provided for this purpose. The catch basin, the footrests located inside it and the pedestal-like base can be designed as a single piece in this context.

The footrests for the parturient are expediently positioned on the inside edge of the catch basin.

Particularly ergonomic positioning of the feet of the parturient on the footrests is possible if the main axes of the footrests are positioned at an angle to each other, where the point of intersection of the axes is on the side of the footrests facing the balloon or ring-shaped bodies. The feet can thus be set on the footrests when the legs are extended and lateral angling of the feet in relation to the legs can be avoided. This enables the parturient to sit in a particularly comfortable position when she presses her feet against the footrests, especially when she sits on the obstetric device in a position where her legs are slightly spread.

A symmetrical arrangement in which the point of intersection of the main axes of the footrests lies on the centre line of the obstetric device is preferred, where the angle of intersection of the main axes is expediently 60°, although this is not to be seen as a restriction.

The pedestal-like base and the catch basin expediently extend, at least partially, between the balloon or ring-shaped bodies. This increases the overall stability of the obstetric device and facilitates the safe receival of the child in the catch basin. A material-saving design of the pedestal-like base is also possible, where it need not have a section which fully encircles the balloon or ring-shaped bodies.

If the end of the pedestal-like base facing the balloon or ring-shaped bodies is at least partially adapted to the shape of the balloon or ring-shaped bodies, a compact design of the obstetric device in accordance with the invention is achieved, on the one hand, and, on the other hand, a contact surface of the catch basin which acts on the balloon or ring-shaped bodies is present which enables a form-fit and thus results in a particularly stable design.

The balloon or ring-shaped bodies can be connected to one another by a rod extending through them and the pedestal-like base can be connected to the rod in a detachable manner. A connection of this kind can be made on the sections of the rod projecting laterally beyond the balloon or ring-shaped bodies, or also on an exposed section of the rod located between the bodies. This increases the stability of the obstetric device, on the one hand, and enables the balloon or ring-shaped bodies to be used as a relaxation device in the preparatory phase of childbirth, on the other hand, where the pedestal-like base can be connected to the rod during the transition to the birth phase and a continuous transition from the preparatory phase to the birth phase can take place without unnecessarily straining the parturient. The rod can be rigid, e.g. made of metal tubing, or also flexible, e.g. made of elastically deformable plastics.

The balloon or ring-shaped bodies are expediently positioned at a distance from one another, where the rod connecting the bodies is designed as a bar located outside the bodies, and the pedestal-like base is connected to the section of the bar located between the bodies in a detachable manner. A device of this kind for detachable connection can, for example, be designed as a projection located on the end facing the balloon or ring-shaped bodies, where the projection reaches over and behind the bar. The pedestal-like base can thus be mounted on the bar by simply hanging the hook-shaped end on the bar. In this context, the area of the projection running in the vertical direction and reaching behind the bar must be dimensioned in such a way that the projection always securely reaches around the bar, even in the case of relatively heavy parturients. The projection can also be designed in such a way that it reaches behind part of the bodies and rests against the rear side of them.

The pedestal-like base can be secured to the rod with a large degree of play in the vertical direction and a small degree of play in the horizontal direction. The small degree of play in the horizontal direction ensures that the pedestal-like base cannot hit against the rod even in the presence of fluctuating contact pressure of the feet of the parturient on the footrests. Allowing a degree of play in the vertical direction ensures the cushioned movement of the balloon or ring-shaped bodies even with parturients of various weights and when the parturient exerts strong pressure on the seat by supporting her feet on the footrests, or when the parturient makes more forceful movements, without the mounting fixture contacting the rod or the contact area between the pedestal-like base and the floor being reduced.

Further advantageous designs of the obstetric device according to the invention are also possible. For example, the two bodies can be provided with annular graduations or ribs, at least in the region of the gap, which serve to reinforce the bodies in the area of the gap and prevent excessive traction of the bodies in the horizontal direction when the parturient sits down. In addition, the rod connecting the bodies to one another can be provided with grips on each of its ends which are mounted on the rod by means of annular flanges. However, the holding grips can also be directly mounted on each of the bodies. This creates further holding points for the parturient sitting on the seat, in addition to the seat and the footrests. The balloon or ring-shaped bodies can be made of plastic, or any other material with adequate elasticity suitable for going through the motions of the parturient, where the bodies can be hollow and filled with air, water, gel, foam or other suitable materials. The shape of the bodies can be designed to be rotationally symmetrical in relation to their connecting line and mirror symmetrical in relation to the centre plane perpendicular to the axis of symmetry.

Figure 2:
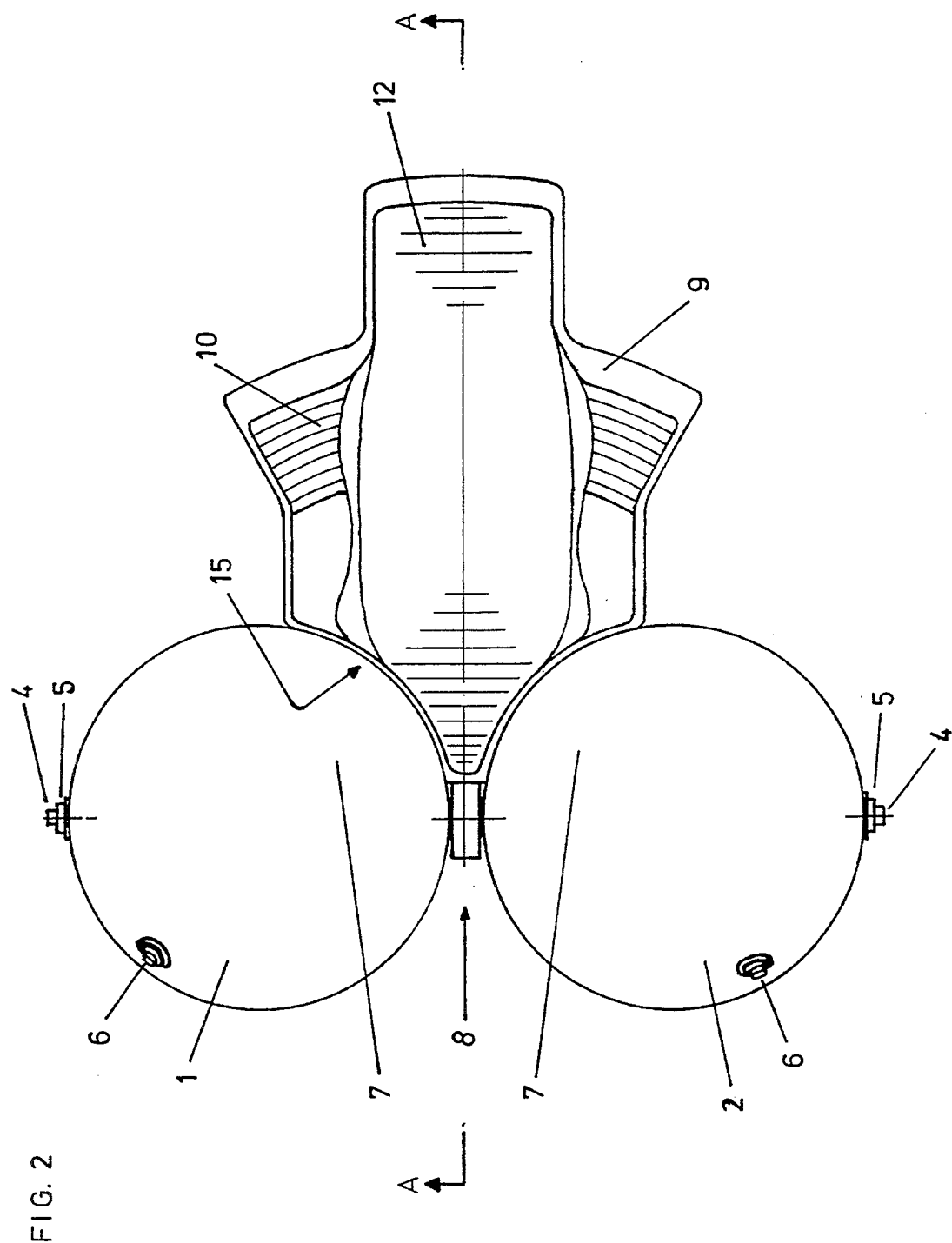
Figure 3:
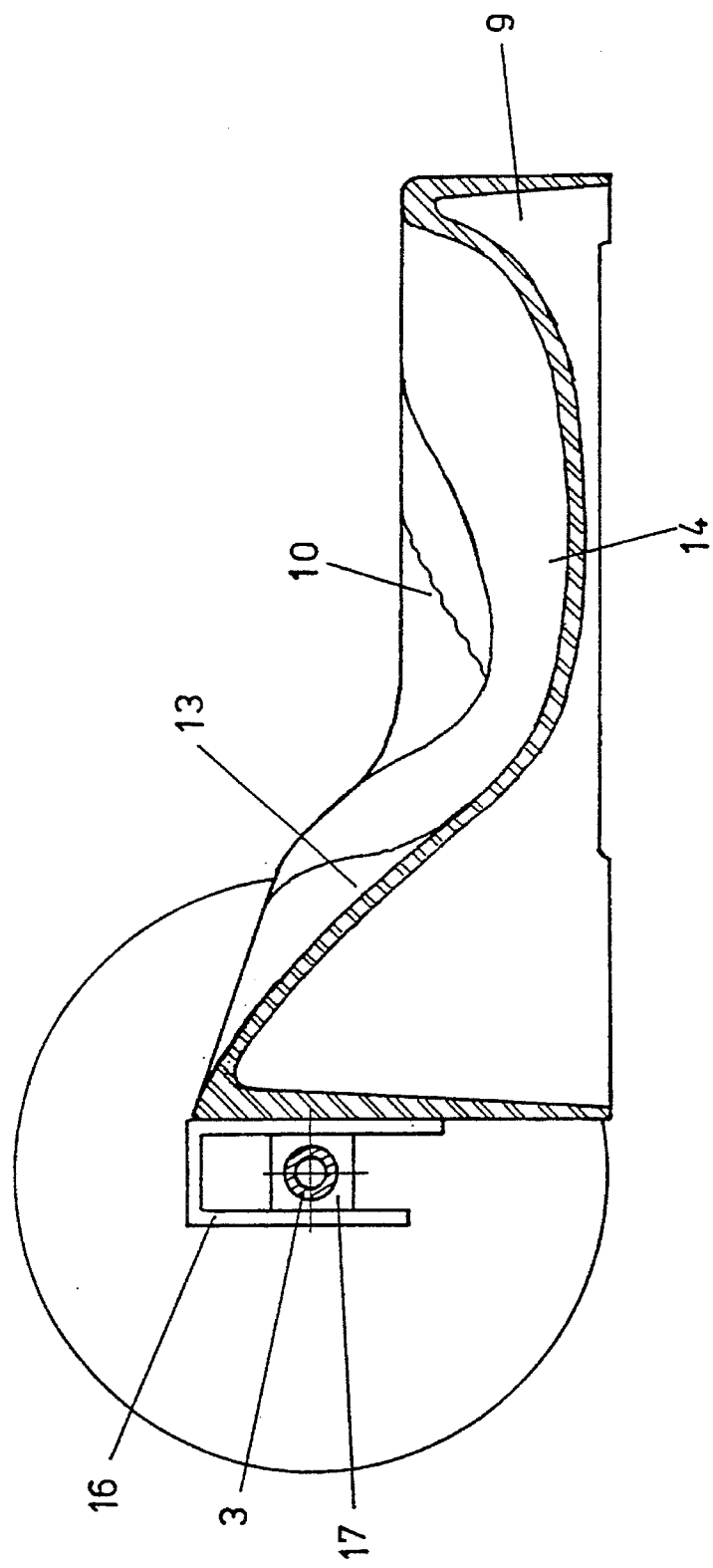

A practical example of the invention is described below in more detail based on the drawings. The drawings show the following:

FIG. 1 a perspective drawing of a childbirth preparation device,

FIG. 2 a top view of the childbirth preparation device shown in FIG. 1,

FIG. 3 a longitudinal section along line A—A of the child-birth preparation device shown in FIG. 2.

As the drawing shows, the obstetric device consists of two spherical bodies 1 and 2 of identical design which are attached to a bar 3 extending through them. The bodies are arranged at a distance from one another, so that the centre region of the bar 3 runs outside the bodies 1 and 2. The two ends of the rigidly designed aluminium bar 3, which project beyond the bodies 1 and 2, are provided with a threaded section 4, onto which a clip 5 is pressed in order to make contact with the regions of the bodies 1 and 2 facing the ends of the bar 3, the bodies 1 and 2 thus being arranged at a specified distance from one another on the bar 3. A sleeve which surrounds the bar 3 and acts as a spacer can be mounted between the bodies 1 and 2. In the present practical example, the bodies 1 and 2 are made of PVC and provided with valves 6, although other practical designs are also possible.

When positioned for use, the bodies 1 and 2 have a region in contact with a floor surface and are dimensioned in this context in such a way that the bar 3 is positioned horizontally. The region of the bodies 1 and 2 facing the space between the bodies 1 and 2 serves as a seat 7 on which the parturient sits during childbirth. A funnel-shaped gap 8 which narrows in the downward direction and is bordered by the spherical surfaces thus extends from the seat 7 and permits access to the vagina of the parturient for examinations and check-ups during the preparatory phase and enables the child to be born to be transferred to the obstetric device during the birth phase.

A pedestal-like base 9 is positioned in front of the bodies 1 and 2 in the sitting direction of the parturient sitting on the seat 7 and is provided with footrests 10 on which the feet of the parturient sitting on the seat 7 can be supported. In this context, the footrests 10 are distanced from the seat and angled vertically relative to the seat 7 in such a way that the parturient can assume a relaxed position and exert contact pressure on the seat 7 with her body with her feet resting on the footrests 10. In addition, the main axes of the footrests 10 are positioned at an angle to one another in the horizontal direction so that the main axes intersect in the region of the bodies 1 and 2 and the parturient sitting on the spheres 1 and 2 with her legs apart can place her feet on the footrests 10 without laterally angling them when her legs are extended (FIG. 2).

In this context, the pedestal-like base 9 is designed as a one-piece plastic moulding, the lower region of which forms a fluid-tight catch basin 11. As FIG. 2 shows, in particular, the footrests 10 are located on the inside of the catch basin 11 and are distanced from one another and from the seat 7 in such a way that the parturient sitting on the seat 7 takes up a relaxed position during the birth phase. In this context, the footrests are integrally moulded as depressions in the edge of the catch basin 11 and provided with a non-slip surface, so that secure and non-slip positioning of the feet on the footrests 10 is ensured, even in the presence of moisture and during exertion of high contact pressure. The catch basin 11 also has a rest area 12 in which the feet of the parturient can also be positioned when her legs are extended, so that the parturient can also put her feet in the respectively desired position before or after childbirth.

The catch basin 11 has a slanted surface 13 on the end facing the bodies 1 and 2, on which the child to be born can safely be transferred from the parturient to the catch basin 11. This is above all achieved by correspondingly dimensioning the inclination of the slanted surface 13 on which the child to be born is transferred to the catch basin 11 in a sliding manner. The end of the slanted surface 13 facing away from the bodies 1 and 2 gradually turns into a depression 14, in which fluids released during birth, such as amniotic fluid or blood, can be collected without them wetting the footrests 10 and increasing the danger of slipping while resting the feet. The slanted surface 13 is of concave form, in order to ensure the uniform downward sliding of the child to be born.

The end of the catch basin 11 facing the bodies 1 and 2 partially extends between the balloon-shaped bodies 1 and 2 up to the gap 8 which narrows in the downward direction and whose bottom end is bordered by the bar 3. Thus, the upper section of the slanted surface 13 which rises towards the balloon-shaped bodies 1 and 2 also extends between the balloon-shaped bodies 1 and 2, so that the slanted surface 13 reaches up close to the parturient sitting on the seat 7 in order to be able to directly receive the child to be born.

The end of the pedestal-like base 9 located between the bodies 1 and 2 has two convexly curved areas 15 facing away from one another on opposite sides, which are adapted to the shape of the adjacent areas of the balloon-shaped bodies 1 and 2, so that the pedestal-like base 9 contacts the bodies 1 and 2 over the largest possible area. A close form-fit of this kind between the pedestal-like base 9 and the bodies 1 and 2 provides for a stable position of the obstetric device during birth and, in particular, reliably prevents the pedestal-like base 9 from overturning in the lateral direction.

The upper end of the pedestal-like base 9 located between the bodies 1 and 2 is provided with a hook-shaped projection 16 which, when the convexly curved surfaces 15 are in contact with the bodies 1 and 2, reaches behind the bar 3 and ensures the stable position of the obstetric device. In order to connect the pedestal-like base 9 to the bar 3, the projection 16 is positioned in such a way that it reaches behind the bar 3. In this context, the projection 16 is flush with the sleeve 17 surrounding the bar 3 in the horizontal direction and has a degree of play relative to the sleeve 17 in the vertical direction.

If the obstetric device according to the invention is put to use, the entire surface of the pedestal-like base 9 facing the floor preferably lies on the floor, in order to ensure the greatest possible stability and slip resistance. In this context, however, it is sufficient for the pedestal-like base 9 to contact the floor at only two points.

Reference Numbers

1 Balloon-shaped body
2 Balloon-shaped body
3 Bar
4 Threaded section
5 Clip
6 Valves
7 Seat
8 Gap
9 Pedestal-like base
10 Footrest
11 Catch basin
12 Rest area
13 Slanted surface
14 Depression
15 Convex contact area
16 Projection
17 Sleeve

I claim:

1. Obstetric device with two balloon or ring-shaped bodies (1, 2) of essentially identical design, which are positioned on an axis which forms the connecting line between the two bodies (1, 2) and runs in the horizontal direction when positioned for use, where the bodies (1, 2) are arranged and connected to one another by connecting means in such a way that, when set down on a floor surface, their upper sections are separated from one another by a gap (8) and their top sides form a seat (7) for a parturient sitting on the two bodies (1, 2), and a pedestal-like base (9) with means to be detachably positioned in an essentially stable, fixed spatial relationship to the balloon or ring-shaped bodies (1, 2), where the pedestal-like base (9) has footrests (10) on which the parturient sitting on the seat (7) can rest her feet, the base (9) being detachably connected to the connecting means in said gap between the two balloon bodies (1, 2).

2. Obstetric device as per claim 1, characterised in that the pedestal-like base (9) has a catch basin (11) for the child to be born.

3. Obstetric device as per claim 2, characterized in that the catch basin (11) is a fluid-tight receptacle.

4. Obstetric device as per claim 2, characterized in that the catch basin (11) has a slanted surface (13) on the end facing the balloon or ring-shaped bodies (1, 2) which rises towards the balloon or ring-shaped bodies (1, 2) which rises towards the balloon or ring shaped bodies (1, 2) and is shaped in such a way that the child to be born can safely slide from the parturient sitting on the seat (7) onto the slanted surface (13) and into the catch basin (11).

5. Obstetric device as per claim 2, characterised in that the footrests (10) are located inside the catch basin (11).

6. Obstetric device as per claim 5, characterised in that the footrests (10) are located on the inside edge of the catch basin (11).

7. Obstetric device as per claim 5, characterized in that the footrests each include a main axis wherein the main axes of the footrests (10) intersect at an angle, where the point of intersection of the axes lies on the side of the footrests (10) facing the balloon or ring-shaped bodies (1, 2).

8. Obstetric device as per claim 2, characterised in that the pedestal-like base (9) and the catch basin (11) extend, at least partially, between the balloon or ring-shaped bodies (1, 2).

9. Obstetric device as per claim 8, characterised in that the end of the pedestal-like base (9) facing the balloon or ring-shaped bodies (1, 2) is at least partially adapted to the shape of the bodies (1, 2).

10. Obstetric device as per claim 1, characterized in that the connecting means comprises a rod (bar 3) extending through the two balloon bodies (1, 2).

11. Obstetric device as per claim 10, characterized in that the pedestal-like base (9) is connected to the rod (bar 3) with a degree of play in the vertical direction preventing the mounting fixture from contacting the rod on vertical movement of the bodies and substantially no play in the horizontal direction.

* * * * *